United States Patent
Sugaya et al.

(10) Patent No.: US 10,832,410 B2
(45) Date of Patent: Nov. 10, 2020

(54) COMPUTER SYSTEM, METHOD, AND PROGRAM FOR DIAGNOSING SUBJECT

(71) Applicants: OPTiM Corporation, Saga (JP); Saga University, Saga (JP)

(72) Inventors: Shunji Sugaya, Tokyo (JP); Yoshio Okumura, Tokyo (JP); Hiroshi Enaida, Saga (JP); Mika Sakaguchi, Saga (JP); Eizaburo Sueoka, Saga (JP)

(73) Assignees: OPTIM CORPORATION, Saga (JP); SAGA UNIVERSITY, Saga (JP)

( * ) Notice: Subject to any disclaimer, the term of this patent is extended or adjusted under 35 U.S.C. 154(b) by 0 days.

(21) Appl. No.: 16/077,790

(22) PCT Filed: May 19, 2017

(86) PCT No.: PCT/JP2017/018840
§ 371 (c)(1),
(2) Date: Aug. 14, 2018

(87) PCT Pub. No.: WO2018/211688
PCT Pub. Date: Nov. 22, 2018

(65) Prior Publication Data
US 2020/0065967 A1    Feb. 27, 2020

(51) Int. Cl.
*G06T 7/00* (2017.01)
*G16H 70/60* (2018.01)
(Continued)

(52) U.S. Cl.
CPC .......... *G06T 7/0016* (2013.01); *G06N 20/00* (2019.01); *G16H 30/20* (2018.01); *G16H 30/40* (2018.01);
(Continued)

(58) Field of Classification Search
None
See application file for complete search history.

(56) References Cited

U.S. PATENT DOCUMENTS

| | | | | |
|---|---|---|---|---|
| 2013/0308824 A1* | 11/2013 | Leung | ......... | G06K 9/0061 382/103 |
| 2017/0091554 A1 | 3/2017 | Miyamoto | | |

FOREIGN PATENT DOCUMENTS

| | | |
|---|---|---|
| JP | 09-330405 | 12/1997 |
| JP | 2005-269214 | 9/2005 |
| JP | 2017-063908 | 4/2017 |

OTHER PUBLICATIONS

Vogl, Wolf-Dieter, et al. "Spatio-temporal signatures to predict retinal disease recurrence."; International Conference on Information Processing in Medical Imaging. Springer, Cham, 2015. (Year: 2015).*

(Continued)

*Primary Examiner* — Vu Le
*Assistant Examiner* — Tracy Mangialaschi
(74) *Attorney, Agent, or Firm* — Lex IP Meister, PLLC (57) ABSTRACT

The present invention is to provide a computer system, a method, and a program for diagnosing a subject that improve the accuracy of diagnosis by combining a plurality of time-series image data more than that by a conventional single image analysis. The computer system for diagnosing a subject acquires a plurality of first subject images with time series variation of the subject, analyzes the acquired first subject images, acquires a plurality of second subject images with time series variation of another subject in the past, analyzes the acquired second subject images, checks the analysis result of the first subject images and the analysis result of the second subject images, and diagnoses the subject based on the check result.

9 Claims, 6 Drawing Sheets

(51) Int. Cl.
  *G16H 30/20* (2018.01)
  *G16H 50/30* (2018.01)
  *G16H 50/20* (2018.01)
  *G06N 20/00* (2019.01)
  *G16H 50/70* (2018.01)
  *G16H 30/40* (2018.01)

(52) U.S. Cl.
  CPC ............ *G16H 50/20* (2018.01); *G16H 50/30* (2018.01); *G16H 50/70* (2018.01); *G16H 70/60* (2018.01); *G06T 2207/20081* (2013.01); *G06T 2207/30041* (2013.01)

(56) References Cited

OTHER PUBLICATIONS

Vogl WD, Waldstein SM, Gerendas BS, Schmidt-Erfurth U, Langs G. Predicting macular edema recurrence from spatio-temporal signatures in optical coherence tomography images. IEEE transactions on medical imaging. May 2, 2017;36(9):1773-83. (Year: 2017).*

Niemeijer, M., et al. "Automated detection and differentiation of drusen, exudates, and cotton-wool spots in digital color fundus photographs for diabetic retinopathy diagnosis.", Investigative ophthalmology & visual science;48.5 (2007): 2260. (Year: 2007).*

Kälviäinen, R. V. J. P. H., and H. Uusitalo. "DIARETDB1 diabetic retinopathy database and evaluation protocol."; Medical Image Understanding and Analysis. vol. 2007. Citeseer, 2007. (Year: 2007).*

Narasimha-Iyer, Harihar, et al. "Robust detection and classification of longitudinal changes in color retinal fundus images for monitoring diabetic retinopathy." IEEE transactions on biomedical engineering 53.6 (2006): 1084-1098. (Year: 2006).*

Narasimha-Iyer, Harihar, et al. "Integrated analysis of vascular and nonvascular changes from color retinal fundus image sequences." IEEE Transactions on Biomedical Engineering 54.8 (2007): 1436-1445. (Year: 2007).*

LPTech, "Accurate image diagnosis by artificial intelligence, Enlitic," Sep. 15, 2016, retrieved on Dec. 22, 2016 from the Internet <URL://htttps://lp-tech.net/articles/TXrrN>.

* cited by examiner

COMPUTER SYSTEM, METHOD, AND PROGRAM FOR DIAGNOSING SUBJECT

TECHNICAL FIELD

The present invention relates to a computer system, a method, and a program for diagnosing a subject.

BACKGROUND ART

Recently, artificial intelligence has been known to be used for image diagnosis (refer to Non-Patent Document 1). In this method, image data is analyzed by deep learning, etc., to identify a disease.

CITATION LIST

Non-Patent Literature

Non-Patent Document 1; LPTech, "Accurate image diagnosis by artificial intelligence, Enlitic," Sep. 15, 2016, retrieved on Dec. 22, 2016 from the Internet <URL:// https://lp-tech.net/articles/TXrrN>

SUMMARY OF INVENTION

However, in the composition of Non-Patent Document 1, a disease and a symptom are identified by not a plurality of image data but only an image datum acquired.

An objective of the present invention is to provide a computer system, a method, and a program for diagnosing a subject that improve the accuracy of diagnosis by combining a plurality of time-series image data more than that by a conventional single image analysis.

The present invention provides a computer system for diagnosing a subject, including;

a first image acquisition unit that acquires a plurality of first subject images with time series variation of the subject;

a first image analysis unit that analyzes the acquired first subject images;

a second image acquisition unit that acquires a plurality of second subject images with time series variation of another subject in the past;

a second image analysis unit that analyzes the acquired second subject images;

a check unit that checks the analysis result of the first subject images and the analysis result of the second subject images; and a diagnosis unit that diagnoses the subject based on the check result.

According to the present invention, the computer system for diagnosing a subject acquires a plurality of first subject images with time series variation of the subject, analyzes the acquired first subject images, acquires a plurality of second subject images with time series variation of another subject in the past, analyzes the acquired second subject images, checks the analysis result of the first subject images and the analysis result of the second subject images, and diagnoses the subject based on the check result.

The present invention is the category of a computer system, but the categories of a method, a program, etc., for diagnosing a subject have similar functions and effects.

The present invention can provide a computer system, a method, and a program for diagnosing a subject that improve the accuracy of diagnosis by combining a plurality of time-series image data more than that by a conventional single image analysis.

DESCRIPTION OF EMBODIMENTS

Embodiments of the present invention will be described below with reference to the attached drawings. However, this is illustrative only, and the technological scope of the present invention is not limited thereto.

Overview of System for Diagnosing a Subject 1

Figure 1:
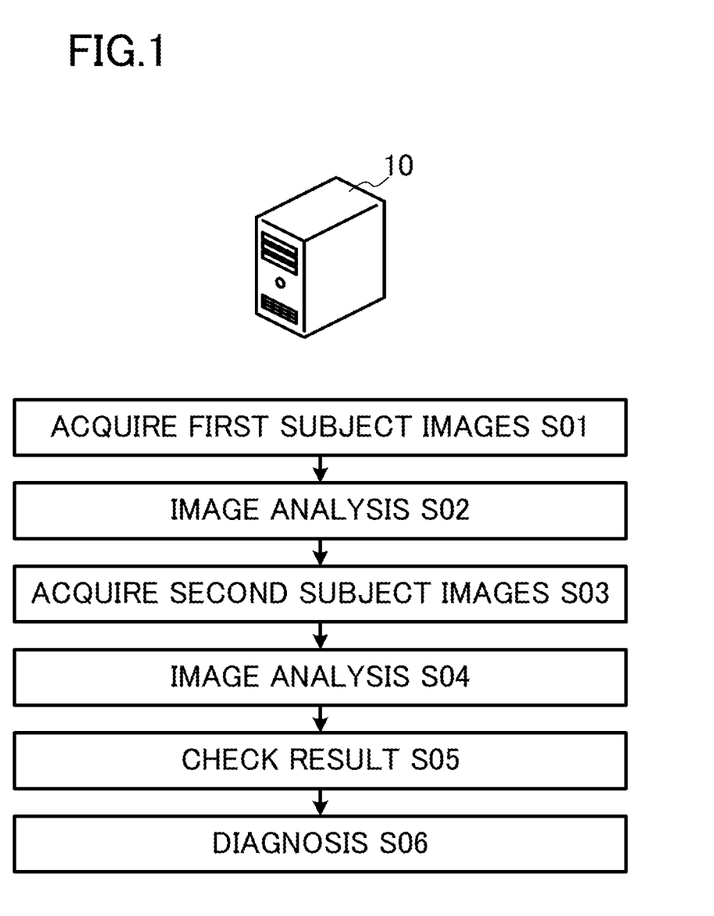
FIG. 1 shows a schematic diagram of the system for diagnosing a subject 1.

A preferable embodiment of the present invention will be described below with reference to FIG. 1. FIG. 1 shows an overview of the system for diagnosing a subject 1 according to a preferable embodiment of the present invention. The system for diagnosing a subject 1 is a computer system including a computer 10 to diagnose a subject.

The following description explains that the system for diagnosing a subject 1 acquires and marks an eye-fundus image, analyzes the marked eye-fundus image, and diagnoses the subject's glaucoma as one example. The subject includes not only a patient but also a healthy person.

The computer 10 is a computing device that is communicatively connected with, for example, various imaging devices (not shown) such as a visible camera, an X-ray camera, a magnetic resonance imaging (hereinafter referred to as "MRI") device, and a computed tomography (hereinafter referred to as "CT") device, a computer (not shown) that stores electronic medical charts, etc., a measuring device that measures vital data, a testing device that performs various tests, and a terminal device that a doctor or a subject owns.

First, the computer 10 acquires a plurality of first subject images with time series variation of a subject (Step S01). The computer 10 acquires any one or a combination of any two or more of eye-fundus images, X-rays images, MRI images, CT scan images, or infrared images as the first subject images. The computer 10 acquires the above-mentioned first subject images imaged by the above-mentioned various imaging devices. The first subject images may not be limited to the above-mentioned images and may be other images.

The computer 10 analyzes the acquired first subject images (Step S02). The computer 10 performs the image analysis by analyzing any one or both of the feature point and the feature amount of the first subject images. The feature point is contained in the images, which is specifically a shape, a color, a brightness, a contour, etc. The feature amount is a statistical numerical value such as a various numerical value (the average, the variance, or the histogram of pixel values) that is calculated from image data.

The computer 10 may previously perform machine-learning on any one or both of the feature point and the feature amount of the second subject images to be described later and analyze the first subject images based on the learning result. The computer 10 may also analyze the first subject images marked (or colored) with a terminal device, etc., which is not shown in the drawings. The marking means coloring each certain part, etc., of an image in a different color.

The computer 10 acquires a plurality of second subject images with time series variation of another subject in the past (Step 03). The computer 10 acquires the second subject images from other computers, databases, etc. that are not shown in the drawings. The computer 10 acquires one or more second subject images.

The computer 10 analyzes the acquired second subject images (Step S04). The computer 10 performs the image analysis by analyzing any one or both of the feature point and the feature amount of the second subject images. The computer 10 analyzes the second subject images in the same way as the above-mentioned first subject images. Specifically, if analyzing the feature point of the first subject images, the computer 10 analyzes the feature point of the second subject images. If analyzing the feature amount of the first subject images, the computer 10 analyzes the feature amount of the second subject images. If analyzing the feature amount and the feature point of the first subject images, the computer 10 analyzes the feature amount and the feature point of the second subject images.

The computer 10 may also analyze the second subject images marked (or colored) with a terminal device, etc., which is not shown in the drawings.

The computer 10 checks the analysis result of the first subject images and the analysis result of the second subject images (Step S05). The computer 10 checks any one or both of the feature point and the feature amount that are analyzed from the first subject images and any one or both of the feature point and the feature amount that are analyzed from the second subject images.

The computer 10 diagnoses the subject based on the check result (Step S06). For example, the computer 10 calculates the degree of similarity between the first subject images and the second subject images based on the check result and diagnoses the subject.

The computer 10 may diagnose the risk of acquiring a disease for the subject based on the check result. The risk of acquiring a disease shows in a number, for example, which estimates how much the subject is likely to be affected with the diagnosed disease in percentage figures.

System Configuration of System for Diagnosing a Subject 1

Figure 2:
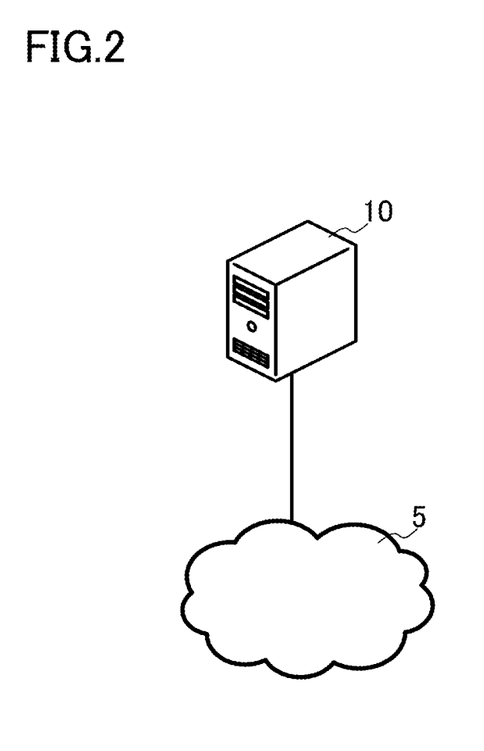
FIG. 2 shows an overall configuration diagram of the system for diagnosing a subject 1.

A system configuration of the system for diagnosing a subject 1 according to a preferable embodiment will be described below with reference to FIG. 2. FIG. 2 shows a block diagram illustrating the system for diagnosing a subject 1 according to a preferable embodiment of the present invention. The system for diagnosing a subject 1 is a computer system including a computer 10 and a public line network 5 (e.g. the Internet network, a third and a fourth generation networks) to diagnose a subject.

The computer 10 is the above-mentioned computing device with the functions to be described later.

Functions

Figure 3:
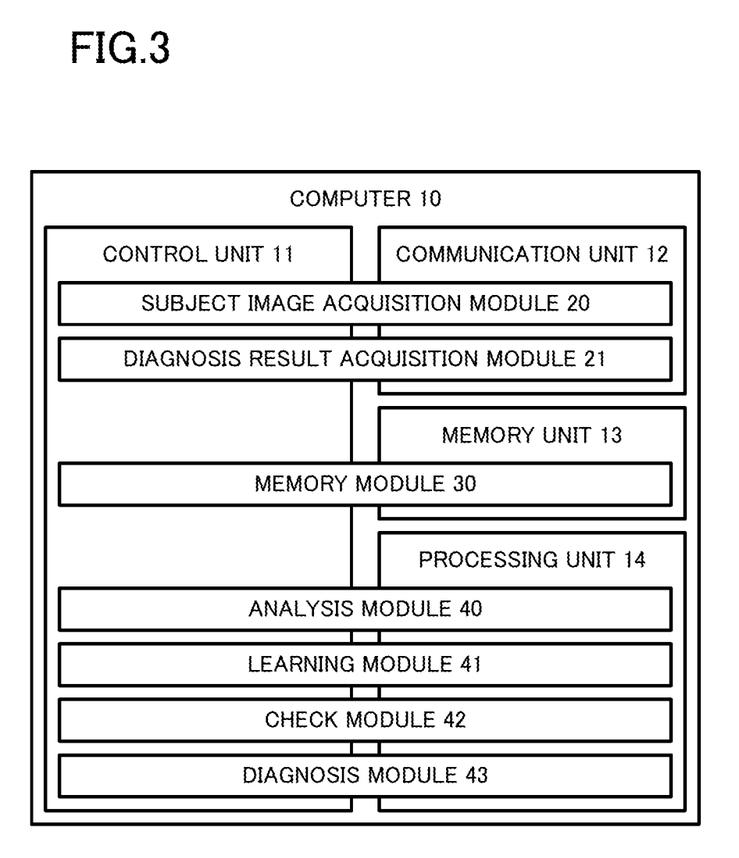
FIG. 3 shows the functional block diagram of the computer 10.

The functions of the system for diagnosing a subject 1 according to a preferable embodiment will be described below with reference to FIG. 3. FIG. 3 shows the functional block diagram of the computer 10.

The computer 10 includes a control unit 11 provided with a central processing unit (hereinafter referred to as "CPU"), a random access memory (hereinafter referred to as "RAM"), and a read only memory (hereinafter referred to as "ROM"); and a communication unit 12 such as a device that is capable to communicate with other devices, for example, a Wireless Fidelity or Wi-Fi® enabled device complying with IEEE 802.11. The computer 10 also includes a memory unit 13 such as a hard disk, a semiconductor memory, a record medium, or a memory card to store data. The computer 10 also includes a processing unit 14 provided with devices that perform various processes such as image processing, status diagnosis, and learning processing.

In the computer 10, the control unit 11 reads a predetermined program to achieve a subject image acquisition module 20 and a diagnosis result acquisition module 21 in cooperation with the communication unit 12. Furthermore, in the computer 10, the control unit 11 reads a predetermined program to achieve a memory module 30 in cooperation with the memory unit 13. Furthermore, in the computer 10, the control unit 11 reads a predetermined program to achieve an analysis module 40, a learning module 41, a check module 42, and a diagnosis module 43 in cooperation with the processing unit 14.

Learning Process

Figure 4:
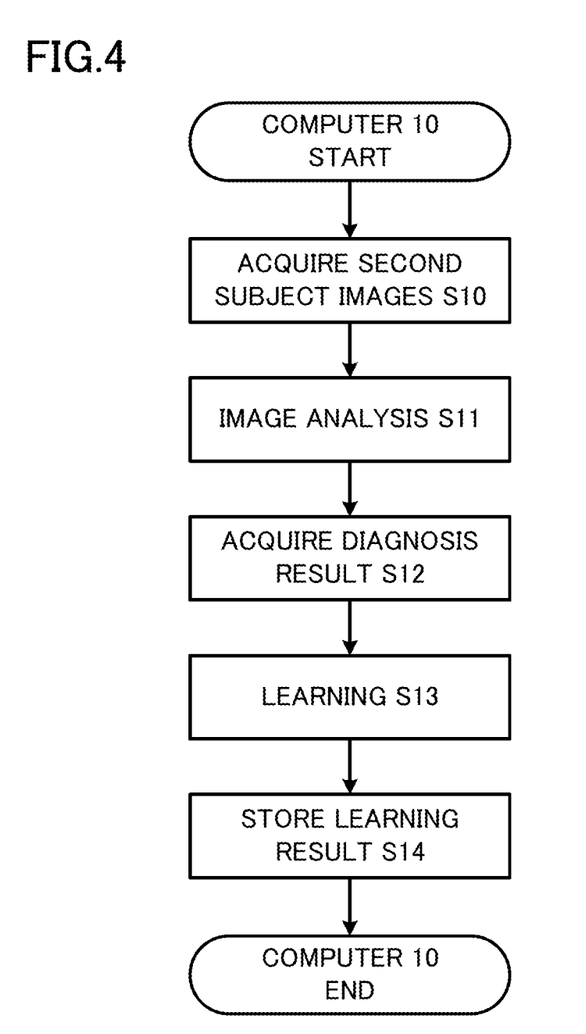
FIG. 4 shows a flow chart illustrating the learning process performed by the computer 10.

The learning process performed by the system for diagnosing a subject 1 will be described below with reference to FIG. 4. FIG. 4 shows a flow chart illustrating the learning process performed by the computer 10. The tasks executed by the modules will be described below with this process.

The subject image acquisition module 20 acquires the given second subject images (Step S10). The second subject images are a plurality of images with time series variation of a subject. In the step S10, the second subject images that the subject image acquisition module 20 acquires are at least one of the eye-fundus images, X-rays images, MRI images, CT scan images, and infrared images of a subject. The subject image acquisition module 20 may acquire the second subject images from the corresponding imaging device, a computer, etc., not shown in the drawings, or a database, etc., stored in this computer, etc. The following description explains the subject image acquisition module 20 acquires eye-fundus images as the second subject images as one example.

The analysis module 40 analyzes any one or both of the feature point and the feature amount of the acquired second subject images (Step S11). The feature point is contained in the second subject images, which is specifically a shape, a color, a brightness, a contour, etc., of an object, etc., contained in the images. The feature amount is a statistical numerical value such as a various numerical value (the average, the variance, or the histogram of pixel values) that is calculated from the second subject images. In the step S11, the analysis module 40 extracts the feature point or the feature amount by analyzing the second subject images. Specifically, the analysis module 40 performs the image analysis by performing the image matching technology, the blob analysis, etc. on the second subject images. The analysis module 40 also extracts the feature amount by performing a predetermined calculation on the second subject images.

The diagnosis result acquisition module 21 acquires the diagnosis result of the acquired subject who corresponds to the second subject images (Step S12). In the step S12, the diagnosis result acquisition module 21 acquires the diagnosis result of the subject associated with the acquired second subject images. The diagnosis result acquisition module 21 acquires the diagnosis result from a computer, etc., not shown in the drawings, or a database, etc., stored in this computer, etc. For example, the diagnosis result in this embodiment identifies the name of a disease, a symptom, a necessary treatment, etc.

The learning module 41 learns the diagnosis result, associating with the second subject images (Step S13). In the step S13, the learning module 41 learns the diagnosis result that the diagnosis result acquisition module 21 acquires, associating with the second subject images that the subject image acquisition module 20 acquires. The learning module 41 learns the diagnosis result, associating with at least one of the eye-fundus images, X-rays images, MRI images, CT scan images, and infrared images of the above-mentioned subject. The learning that the learning module 41 performs is the machine learning that learns repeatedly from data and finds a pattern from the learning.

In the above-mentioned steps S11 to S13, the learning module 41 may learn the diagnosis result, associating with the second subject images based on the second subject images that are colored with a terminal device, etc., (not shown) that a healthcare worker owns, without the analysis module 40 extracting any one or both of the feature point and the feature amount. In this case, the analysis module 40 learns the diagnosis result, associating with the marked (or colored) second subject images.

Each of the second subject images is marked by the above-mentioned terminal device, etc. The analysis module 40 analyzes the marked images. The analysis module 40 extracts any one or both of the feature point and the feature amount of a marked part. The analysis module 40 may extract the area, the shape, etc., of the marked part as the feature point and the feature amount.

The memory module 30 stores the learning result (Step S14).

The system for diagnosing a subject 1 performs the above-mentioned learning process sufficient number of times and stores the learning result.

Subject Diagnosis Process

Figure 5:
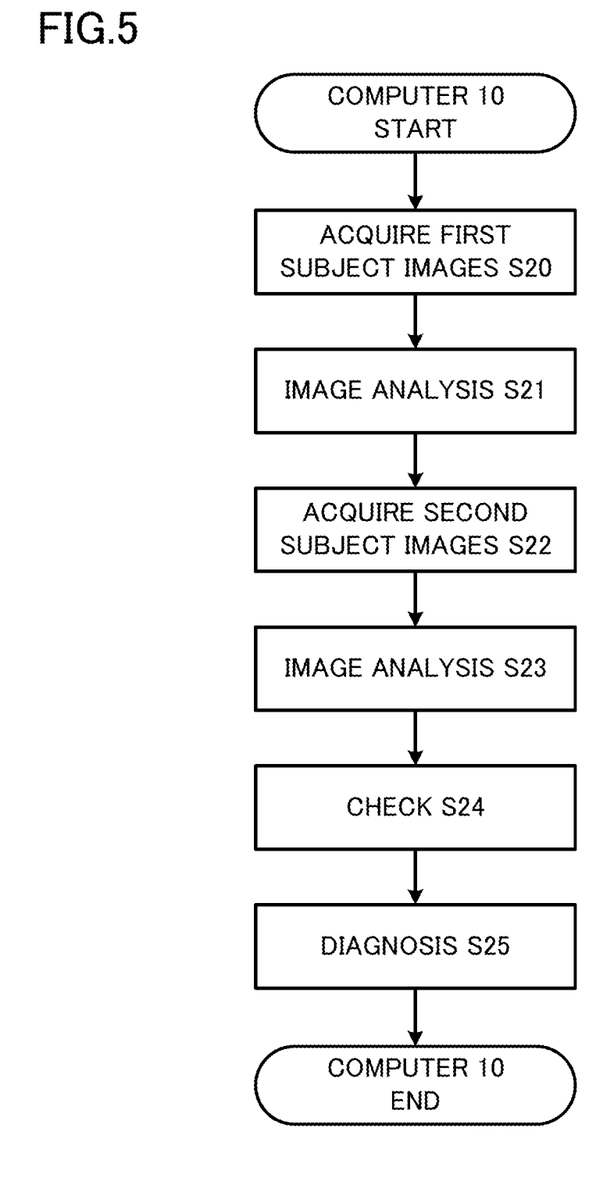
FIG. 5 shows a flow chart illustrating the subject diagnosis process performed by the computer 10.

The subject diagnosis process performed by the system for diagnosing a subject 1 will be described below with reference to FIG. 5. FIG. 5 shows a flow chart illustrating the subject diagnosis process performed by the computer 10. The tasks executed by the modules will be described below with this process. The following description explains that the system for diagnosing a subject 1 diagnoses a subject based on eye-fundus images as one example.

The subject image acquisition module 20 acquires the first subject images (Step S20). The first subject images are a plurality of images with time series variation of a subject. In the step S20, the first subject images that the subject image acquisition module 20 acquires are at least one of the eye-fundus images, X-rays images, MRI images, CT scan images, and infrared images of a subject. The subject image acquisition module 20 may acquire the first subject images from the corresponding imaging device, a computer, etc., not shown in the drawings, or a database, etc., stored in this computer, etc. Specifically, the subject image acquisition module 20 collectively acquires the past images (for example, stored in a computer, etc., not shown in the drawings) and the images taken by an imaging device, etc. this time in line with time series variation as the first subject images. The following description explains that the subject image acquisition module 20 acquires eye-fundus images as the first subject images as one example.

The analysis module 40 analyzes any one or both of the feature point and the feature amount of the acquired first subject images (Step S21). The feature point and the feature amount are as described above. The analysis module 40 extracts the feature point or the feature amount of the first subject images in the same way as the above-mentioned step S11. The analysis module 40 analyzes the marked (or colored) first subject images. The marked first subject images contain each certain part, etc., colored in a different color. The mark is made by a terminal device, etc., not shown in the drawings or automatically made. The analysis module 40 extracts the feature point or the feature amount of each colored part of the marked first subject images.

The subject image acquisition module 20 acquires the second subject images (Step S22). In the step S22, the subject image acquisition module 20 acquires the learning results stored in the memory module 30 in the above-mentioned step S14 as the second subject images. The second subject images that the subject image acquisition module 20 acquires this time are marked.

The subject image acquisition module 20 may not acquire learning results but a plurality of second subject images with time series variation of another subject in the past as the second subject images. Furthermore, the subject image acquisition module 20 may acquire unmarked second subject images.

The analysis module 40 analyzes any one or both of the feature point and the feature amount of the acquired second subject images (Step S23). The step S23 extracts the feature point or the feature amount of the second subject images in the same way as the above-mentioned steps S11 and S21.

The check module 42 checks the analysis result of the first subject images and the analysis result of the second subject images (Step S24). In the step S24, the check module 42 checks any one or both of the feature point and the feature amount that are extracted from the first subject images and any one or both of the feature point and the feature amount that are analyzed from the second subject images. If extracting the feature point from the first subject images, the check module 42 checks the feature point of the first subject images and the feature point of the second subject images. If extracting the feature amount from the first subject images, the check module 42 checks the feature amount of the first subject images and the feature amount of the second subject images in the same way. If extracting the feature point and the feature amount from the first subject images, the check module 42 checks the feature point and the feature amount of the first subject images and the feature point and the feature amount of the second subject images in the same way. The specific check method will be described below.

Figure 6:
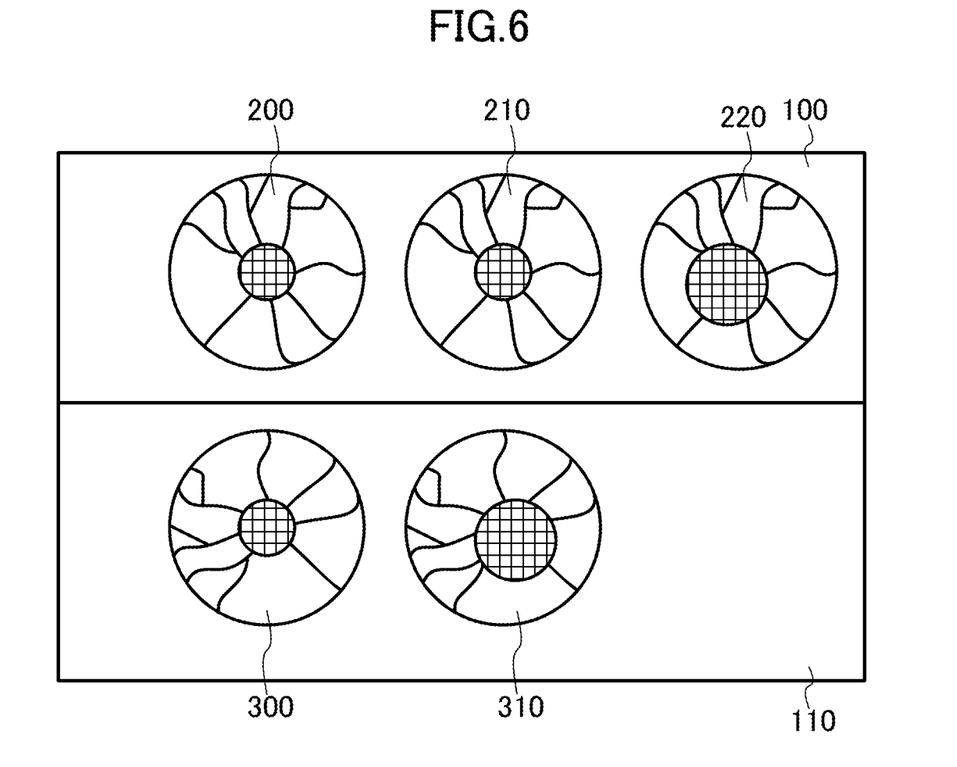
FIG. 6 shows a diagram to illustrate the first subject images and the second subject images that the computer 10 checks.

The first subject images and the second subject images that the check module 42 checks will be described with reference to FIG. 6. FIG. 6 shows a diagram to illustrate the first subject images and the second subject images that the check module 42 checks. In FIG. 6, the check module 42 arranges the first subject images (the first eye-fundus image 200, the second eye-fundus image 210, and the third eye-fundus image 220) in the first subject image display area 100 and the second subject images (the fourth eye-fundus image 300 and the fifth eye-fundus image 310) in the second subject image display area 110 to check. The first eye-fundus image 200, the second eye-fundus image 210, and the third eye-fundus image 220 show a subject in time series. The fourth eye-fundus image 300 and the fifth eye-fundus image 310 differs from the first subject images and show another subject in the past in time series. The fifth eye-fundus image 310 shows that glaucoma is developed. The check module 42 checks the variation from the fourth eye-fundus image 300 to the fifth eye-fundus image 310 with the first subject images as the feature point and the feature amount. The check module 42 checks how much degree of similarity between the variations in the first subject images and in the second subject images are as a score. The higher degree of similarity is determined as a higher score, and the lower degree of similarity is determined as a lower score. The check module 42 checks the variation in the first subject images as the feature point or the feature amount and judges whether or not the subject develops glaucoma by judging whether or not the degree of similarity to the eye-fundus images in the second subject images that show that glaucoma is developed is determined as a high score.

The numbers of the first subject images and the second subject images that the check module 42 checks are not limited to the above-mentioned numbers and can be appropriately changed. The check module 42 may check other subject images in addition to the first subject images and the second subject images.

The diagnosis module 43 diagnoses the subject based on the check result (Step S25). In the step S25, the diagnosis module 43 diagnoses the subject based on the degree of similarity that the check module 42 calculates. As the check result, for example, if the degree of similarity has a score equal to or more than a predetermined value, the diagnosis module 43 diagnoses the subject on the same or similar diagnosis result from the second subject images. The diagnosis module 43 may diagnose the name of a disease and a treatment as a diagnosis result or may diagnose the risk of acquiring a disease. For example, the risk of acquiring a disease estimates the probability of being affected with the diagnosed disease now or in the future in percentage.

As the check result, for example, if the degree of similarity has a score less than a predetermined value, the diagnosis module 43 diagnoses the subject on another diagnosis result by checking other second subject images.

To achieve the means and the functions that are described above, a computer (including a CPU, an information processor, and various terminals) reads and executes a predetermined program. For example, the program may be provided through Software as a Service (SaaS), specifically, from a computer through a network or may be provided in the form recorded in a computer-readable medium such as a flexible disk, CD (e.g., CD-ROM), or DVD (e.g., DVD-ROM, DVD-RAM). In this case, a computer reads a program from the record medium, forwards and stores the program to and in an internal or an external storage, and executes it. The program may be previously recorded in, for example, a storage (record medium) such as a magnetic disk, an optical disk, or a magnetic optical disk and provided from the storage to a computer through a communication line.

The embodiments of the present invention are described above. However, the present invention is not limited to the above-mentioned embodiments. The effect described in the embodiments of the present invention is only the most preferable effect produced from the present invention. The effects of the present invention are not limited to those described in the embodiments of the present invention.

REFERENCE SIGNS LIST

1 System for diagnosing a subject
10 Computer

What is claimed is:

1. A computer system, comprising:
one or more processors that:
acquire a plurality of first subject images with time series variation of a subject;
analyze each of colored certain parts included in each of the acquired first subject images, each of the colored certain parts in each of the acquired first subject images being marked in a different color, and a same certain part of the acquired first subject images being marked in a same color;
acquire a plurality of second subject images with time series variation of another subject in the past;
analyze each of colored certain parts included in each of the acquired second subject images, each of the colored certain parts in each of the acquired second subject images being marked in a different color, and a same certain part of the acquired second subject images being marked in a same color;
check the analysis result of the first subject images and the analysis result of the second subject images; and
diagnose the subject based on the check result,
wherein the one or more processors calculate a degree of similarity between the first subject images and the second subject images based on the check result and diagnoses the subject, and
wherein the one or more processors, when the degree of similarity is less than a predetermined value,
acquire a plurality of third subject images with time series variation of yet another subject in the past,
analyze each of colored certain parts included in each of the acquired third subject images, each of the colored certain parts in each of the acquired third subject images being marked in a different color, and a same certain part of the acquired third subject images being marked in a same color,
further check the analysis result of the first subject images and the analysis result of the third subject images, and
diagnose the subject based on the further check result.

2. The computer system according to claim 1, wherein the one or more processors check a feature point of each of the colored certain parts in the first subject images and a feature point of each of the colored certain parts in the second subject images.

3. The computer system according to claim 1, wherein the one or more processors check a feature amount of each of the colored certain parts in the first subject images and a feature amount of each of the colored certain parts in the second subject images.

4. The computer system according to claim 1, wherein the one or more processors diagnose a risk of acquiring a disease for the subject based on the check result.

5. The computer system according to claim 1, wherein the one or more processors perform machine-learning on a feature point of the second subject images and analyzes the acquired first subject images.

6. The computer system according to claim 1, wherein the one or more processors perform machine-learning on a feature amount of the second subject images and analyzes the acquired first subject images.

7. The computer system according to claim 1, wherein the first subject images are eye-fundus images, the one or more processors analyze the acquired eye-fundus images which are marked, and diagnose the subject's glaucoma.

8. A method for diagnosing a subject by a computer system, comprising:
acquiring a plurality of first subject images with time series variation of the subject;
analyzing each of colored certain parts included in each of the acquired first subject images, each of the colored certain parts in each of the acquired first subject images being marked in a different color, and a same certain part of the acquired first subject images being marked in a same color;
acquiring a plurality of second subject images with time series variation of another subject in the past;

analyzing each of colored certain parts included in each of the acquired second subject images, each of the colored certain parts in each of the acquired second subject images being marked in a different color, and a same certain part of the acquired second subject images being marked in a same color;

checking the analysis result of the first subject images and the analysis result of the second subject images; and diagnosing the subject based on the check result, the method further comprising:

calculating a degree of similarity between the first subject images and the second subject images based on the check result; and when the degree of similarity is less than a predetermined value, acquiring a plurality of third subject images with time series variation of yet another subject in the past, analyzing each of colored certain parts included in each of the acquired third subject images, each of the colored certain parts in each of the acquired third subject images being marked in a different color, and a same certain part of the acquired third subject images being marked in a same color, further checking the analysis result of the first subject images and the analysis result of the third subject images, and diagnosing the subject based on the further check result.

9. A non-transitory computer-readable medium comprising instructions that when executed by a computer system cause the computer system to execute acquiring a plurality of first subject images with time series variation of the subject;

analyzing each of colored certain parts included in each of the acquired first subject images, each of the colored certain parts in each of the acquired first subject images being marked in a different color, and a same certain part of the acquired first subject images being marked in a same color;

acquiring a plurality of second subject images with time series variation of another subject in the past;

analyzing each of colored certain parts included in each of the acquired second subject images, each of the colored certain parts in each of the acquired second subject images being marked in a different color, and a same certain part of the acquired second subject images being marked in a same color;

checking the analysis result of the first subject images and the analysis result of the second subject images; and diagnosing the subject based on the check result, wherein the instructions cause the computer system to further execute:

calculating a degree of similarity between the first subject images and the second subject images based on the check result; and when the degree of similarity is less than a predetermined value, acquiring a plurality of third subject images with time series variation of yet another subject in the past, analyzing each of colored certain parts included in each of the acquired third subject images, each of the colored certain parts in each of the acquired third subject images being marked in a different color, and a same certain part of the acquired third subject images being marked in a same color, further checking the analysis result of the first subject images and the analysis result of the third subject images, and diagnosing the subject based on the further check result.

* * * * *